(12) United States Patent
O'Donnell, Jr.

(10) Patent No.: US 6,197,018 B1
(45) Date of Patent: Mar. 6, 2001

(54) LASER METHOD FOR RESTORING ACCOMMODATIVE POTENTIAL

(76) Inventor: Francis E. O'Donnell, Jr., 709 The Hamptons La., Town & Country, MO (US) 63017

( * ) Notice: Subject to any disclaimer, the term of this patent is extended or adjusted under 35 U.S.C. 154(b) by 0 days.

(21) Appl. No.: 09/324,202

(22) Filed: Jun. 2, 1999

Related U.S. Application Data

(63) Continuation-in-part of application No. 08/910,086, filed on Aug. 12, 1997, now abandoned.
(60) Provisional application No. 60/023,249, filed on Aug. 12, 1996.

(51) Int. Cl.$^7$ .................................................. A61B 18/18
(52) U.S. Cl. ................................................ 606/4; 606/13
(58) Field of Search ...................... 606/4, 5, 13; 128/898

(56) References Cited

U.S. PATENT DOCUMENTS 6,099,522 * 8/2000 Knopp et al. ........................ 606/10

* cited by examiner

Primary Examiner—Linda C. M. Dvorak
Assistant Examiner—Roy Gibson
(74) Attorney, Agent, or Firm—Paul M. Denk

(57) ABSTRACT

Presbyopia correction is achieved by a tightening of the crystalline lens capsule. Applying laser energy to the pre-equatorial lens capsular membrane in increase the capsule tension without unwanted effects on the central clarity or on the refractive status of the eye. Wavelength selection, power, pulse duration, treatment spot size, placement, and pattern affect the accommodative and refractive effect.

12 Claims, 2 Drawing Sheets

LASER METHOD FOR RESTORING ACCOMMODATIVE POTENTIAL

CROSS-REFERENCE TO RELATED APPLICATIONS

This application is a continuation-in-part application of application Ser. No. 08/910,086, filed Aug. 21, 1997, now abandoned, which claimed priority to the provisional patent application Ser. No. 60/023,249, filed Aug. 12, 1996.

BACKGROUND OF THE INVENTION

This invention is directed generally to the correction of vision and, more specifically to the reversing the effects of aging on accommodation by increasing the tension of the capsular membrane.

The normal aging process is associated with a loss of accommodative potential (presbyopia). This loss of accommodation requires the use of corrective lenses in order to perform visual tasks at near, such as reading.

Moreover, many patients have a hyperopic refractive error for which they compensate by using their accommodative potential when they are young. As they grow older, therefore, they more easily exhaust their accommodative reserve resulting in a biphasic pattern of increased dependence on optical appliances. Initially, they develop a need for corrective lenses just for near work; but eventually, they need corrective lenses for distances as well.

Patients with low to moderate myopia can compensate for presbyopia by removing their corrective lenses for near work. With the introduction of effective means for correcting myopia by photorefractive keratectomy (PRK), these patients forfeit the option when they elect to have their myopia eliminated.

The etiology of presbyopia has not been firmly established. Contributing factors identified to date include an apparent loss of ciliary muscle function, sclerosis of the crystalline lens fibers, loss of capsular tension by reduced elasticity, and crowding of the anterior segment of the eye by continued growth of the crystalline lens after puberty.

Recently, a method of restoring accommodative amplitude by expanding the equatorial circumference of the globe over the ciliary body by a variety of surgical techniques has been disclosed. These surgical techniques are quite invasive requiring deep invasions in the eyeball or the suturing of an expansive band to the eyeball.

SUMMARY OF THE INVENTION

One object of the present invention is to provide a method of performing a non-invasive alteration of the lens capsular membrane tension by the application of laser energy restoring the accommodative potential.

Another object of the invention includes the use of the appropriate laser energy that can be used to restore the accommodative potential of the ocular lens with or without a concomitant change in refractive error through usage of this procedure.

Another object of the invention is to control the laser wave length for providing an adequate transmission to the target plane of the lens capsular membrane by selecting a focal spot size of sufficient size to effect a local contractor of the lens capsular membrane.

Yet another object of the invention is provide a method for placing a symmetrical pattern of spots to avoid induction of lenticular astigmatism, and by accurate placement of the spots away from these pupillary space to avoid optical side effects.

Another object of the invention is to provide for the restoration of accommodative reserve by the use of an infrared laser to cause a tightening of the lens capsular membrane.

Another object of this invention is to provide the method for achieving such restoration, as aforesaid, wherein the laser wave length selected is in the near infrared range of 800 nm to 1900 nm.

Yet another object of this invention is to provide a method wherein the laser is a continuous wave laser delivered in a pulsed fashion for a duration of 0.01 second to 1 second per spot application.

Yet another object of this invention is to provide the method for restoration wherein the laser spot size is selected to be between 100 to 500 microns in diameter.

Still another object of this invention is to provide the method for restoration wherein the laser energy per spot application is in the range of 50 mW to 1,000 mW.

Yet another object of this invention is to provide a method for restoration of the accommodative reserve of the lens wherein the treatment spots are arranged in a symmetrical fashion along a circle or concentric circles of 7 mm to 13 mm in diameter.

Still another object of this invention is to provide a method of restoration of the accommodative reserve of the lens wherein the hyperoptic refractive error is concurrently corrected (myopic shift) by placing the spots closer to the pupil center.

Yet another object of this invention is to provide a method for restoration wherein an astigmatic refractive error is concurrently corrected by placing additional spots closer to the pupil center along the flat meridian.

Yet another object of this invention is to provide the method for restoration wherein the spot intensity is increased along the flat meridian to compensate for unwanted astigmatism.

Another method of this invention is to provide for restoration wherein the laser energy is precisely focused onto the interior or posterior lens capsule.

In accordance with the invention, generally stated, the present invention provides a method of presbyopia correction comprising the tightening or tensioning of the crystalline lens capsule by applying laser energy to the pre-equatorial lens capsular basement membrane, the capsule tension is increased without unwanted effects on the central clarity or on the refractive status of the eye. Wavelength selection, power, pulse duration, treatment spot size, placement, and pattern affect the accommodative and refractive effect.

Other objects and advantages may become more apparent to those skilled in the art upon reviewing this summary of the invention, in view of the description of the preferred embodiment.

DESCRIPTION OF THE PREFERRED EMBODIMENT

Figure 1:
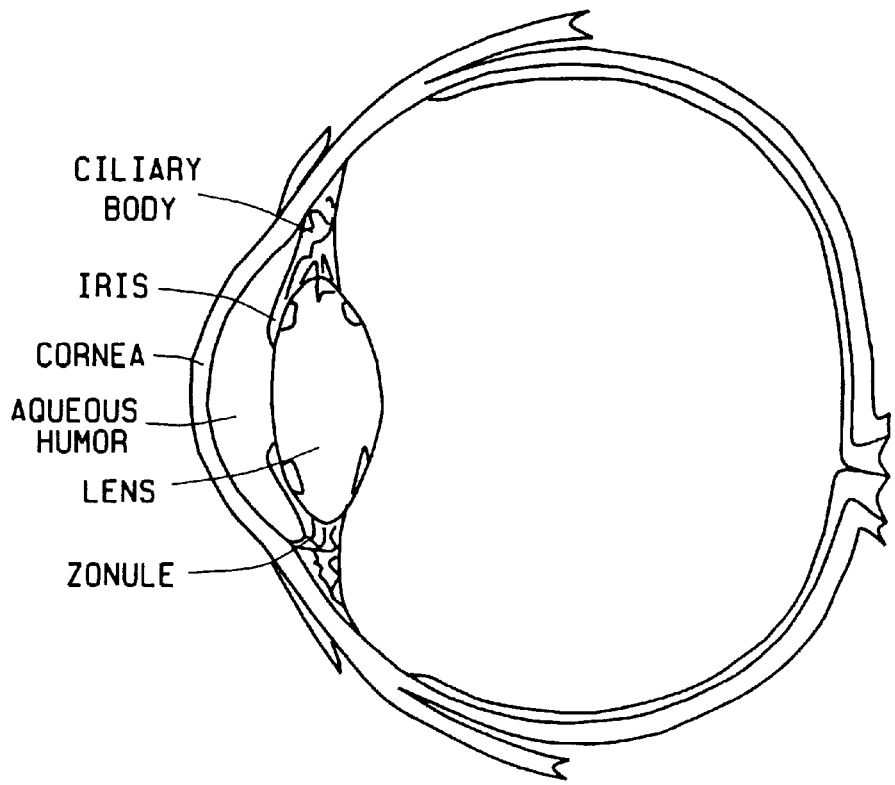
FIG. 1 is a schematic sketch of the eye showing the location of the anterior and posterior capsule treatment spots of the lens.

The inventor has determined that appropriate laser energy application can be used to restore accommodative potential with or without a concomitant change in refractive error. This effect is achieved by controlling the laser wavelength to provide adequate transmission to the target plane of the lens capsule, by selecting a focal spot size of sufficient size to effect a local contracture of the lens capsule by placing a symmetrical pattern of spots to avoid induction of lenticular astigmatism, and by accurate placement of the spots away from the pupillary space to avoid optical side effects.

In one preferred embodiment, the laser energy source is a continuous wave (CW) infrared laser, such as a diode laser, neodynium; YAG laser, or holmium laser Thus, wavelength selection from 800 nm to 1,980 nm is preferred. The CW laser is pulsed to provide a controlled photocoagulation effect. Pulse duration of 0.01 to 1 second is used. Short pulse duration in the nanosecond range or less is avoided in order to eliminate a photodisruption effect. It will be appreciated that the laser energy is directed to the capsular basement membrane in order to increase tension of the capsular membrane and to effect an increased tensioning of the capsular membrane. The basement membrane is comprised of elastin fibers, as well as collagen. The laser energy must be directed through the cornea and through the anterior chamber including the aqueous humor. Hence, the preferred wavelength of laser energy is one that is not absorbed by water.

In another preferred embodiment, the power selected is in the range of 50 mW to 1,000 mW. The energy selection is dependent in part on the wavelength selected with the longer IR wavelengths achieving their thermal coagulative effects with less energy. In addition, patient age and degree of lenticular sclerosis also determine energy requirement. For example, nuclear scientific sclerotic lenses require more energy to achieve the same effect.

In another preferred embodiment, the treatment spot size is selected in the 100–500 micron in diameter range. This size is large enough to effect a local contracture of the lens capsule, but small enough to allow for symmetric placement around the pre-equatorial lens capsular basement membrane.

In another preferred embodiment, the laser energy is precisely focused on the lens capsular basement membrane in order to limit unwanted local cataract (opacity) formation. Although either the anterior or the posterior lens capsule can be used, the anterior capsule is preferable because of ease of focus. Hence, in a preferred embodiment the laser wavelength that is not highly absorbed by water, is directed to the basement membrane of the anterior capsule. Nevertheless, the curvature of the posterior lens capsule is much greater allowing for larger effects for the same degree of capsule contracture. Moreover, it is important to avoid disrupting the lens capsule which could lead to uveitis and progressive cataract formation.

Figure 2A:
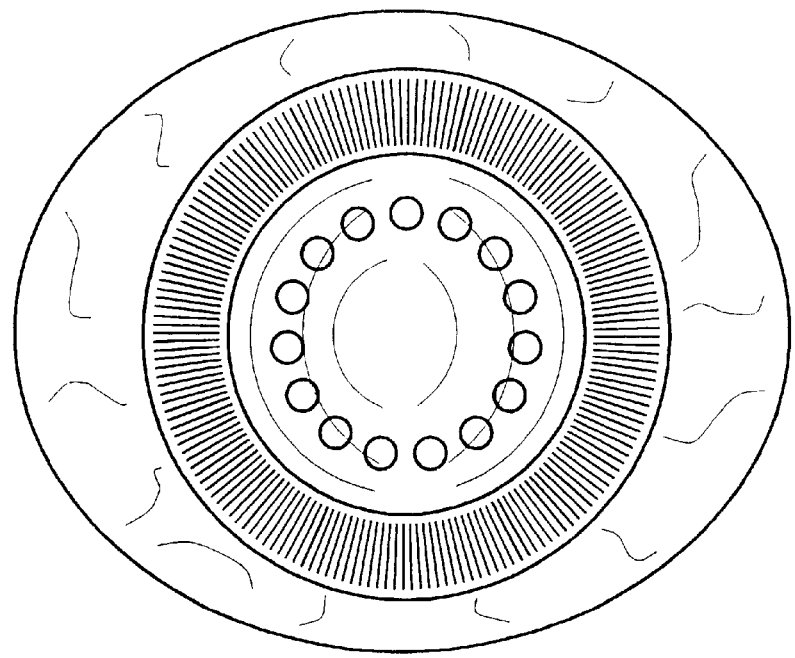
FIG. 2A is a front view showing the array of spots arranged around a particular circumference of the lens.
Figure 2B:
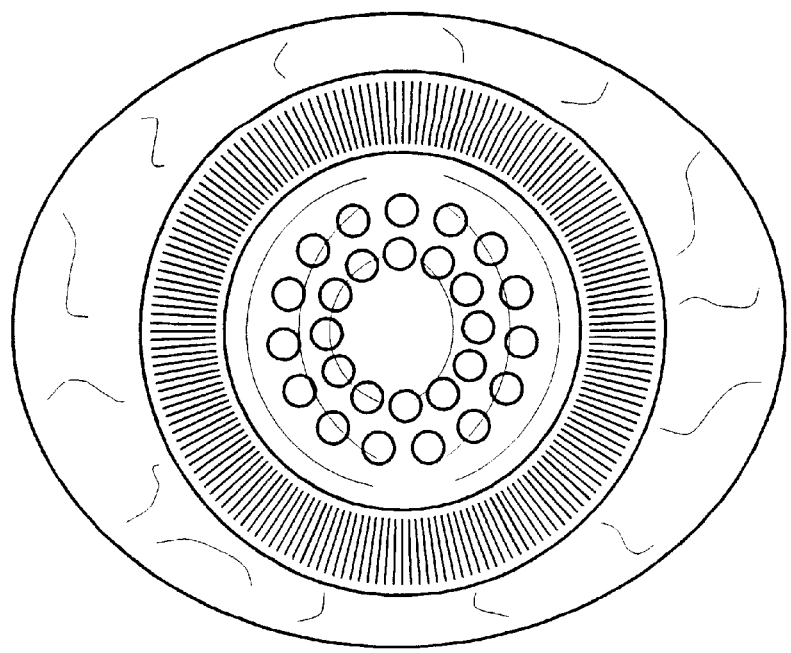
FIG. 2B discloses a dual array of spots provided around a pair of circumferences at predetermine diameters around the lens of the eye.
Figure 2C:
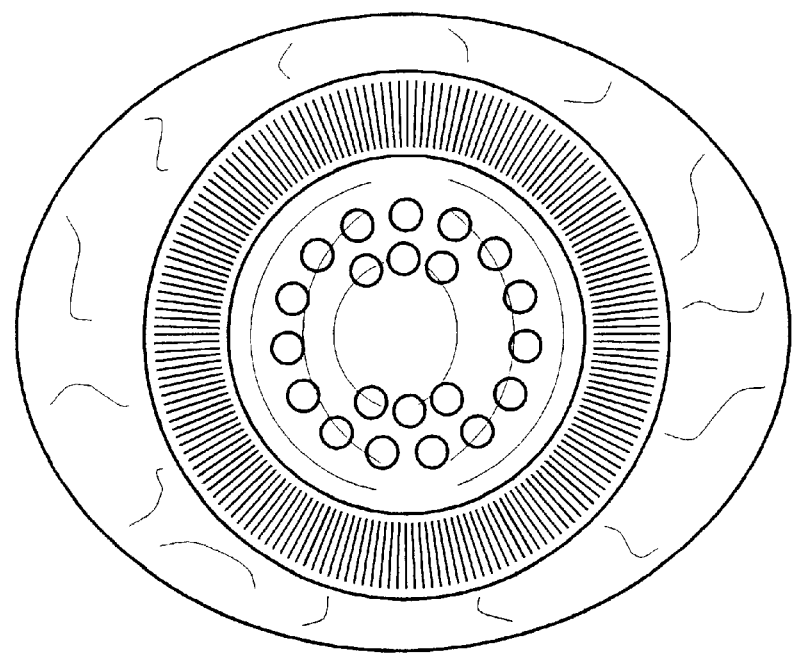
FIG. 2C discloses the spacing of arranged spots at two diameters around the circumference of the lens of the eye.

In another preferred embodiment, the spots are placed with the pupil pharmacologically dilated. The spots are placed peripheral to the scotopic pupil position (typically along a circle 7 mm or more in diameter), but central to the equatorial region of the lens (typically 11–13 mm in diameter) (FIG. 1). By placing the spots closer to the pupil edge, a greater effect on the refractive status of the non-accommodative eye is achieved. That is to say, the smaller the distances from the pupillary spaces, the greater the myopic shift. This is caused by a central steepening of the lens curvature. The spots can be placed in concentric circles (FIG. 2B, 2C).

In another preferred embodiment, the spots are placed symmetrically in order to avoid creation of a lenticular astigmatism at rest or upon accommodation. (FIG. 2B). Conversely, if a pre-existing astigmatism is present, the spot's placement can be oriented so as to neutralize (correct) the astigmatism. By placing extra spots only increasing spot intensity along the flat meridian, extra steepening is achieved to neutralize the astigmatism. (FIG. 2C).

Variations or modifications to the subject matter of this invention may occur to those skilled in the art upon reviewing the subject matter of this disclosure. Such variations or modifications, if within the spirit of this invention, are intended to be encompassed within the scope of this development.

What is claimed is:

1. A method for restoring accommodative potential of an ocular lens of a human eye; the method comprising;

applying laser energy to the lens capsule in a predetermined pattern peripheral to a scotopic pupil position but central to the equatorial region of the lens so as to avoid an optical side effect on the pupil;

wherein the laser energy is directed of the lens capsule.

2. The method of claim 1 wherein the laser energy is directed to the basement capsular membrane of the lens capsule through an anterior chamber of the human eye.

3. The method of claim 1 wherein the step of applying laser energy to the lens capsule comprises applying the laser energy to the lens capsule in a symmetrical pattern generally in a concentric pattern from approximately 7 mm to approximately 13 mm about the pupil.

4. The method of claim 1 wherein the step of applying laser energy to the lens capsule comprises applying the laser energy as a series of spots.

5. The method of claim 2 wherein the step of applying laser energy to the lens capsule comprises applying the laser energy as a symmetrical pattern.

6. The method of claim 1 wherein the laser energy is a wavelength that is not highly absorbed by water.

7. The method of claim 3 wherein the symmetrical pattern comprises a circle of about 7 mm to about 13 mm in diameter.

8. The method of claim 2 wherein the spots are about 100 to about 500 microns in diameter.

9. The method of claim 2 wherein the laser energy per spot application is about 500 mW to about 1000 mW.

10. The method of claim 2 wherein the laser is a continuous wave laser delivered in pulses of about 0.01 second to about 1 second per spot application.

11. The method of claim 1 wherein the laser energy is applied after the pupil of the eye is pharmacologically dilated.

12. A non-invasive method of for restoring accommodative potential of an ocular lens of a human eye comprising:

dilating the pupil of the eye;

applying laser energy in the range of approximately 800 nm to approximately 1980 nm at a pulse duration of approximately 0.01 to 1 second in a concentric pattern of spots of approximately 100 micron to approximately 500 micron in diameter about the pupil of the eye, peripheral to the scotopic pupil at approximately 7 mm to approximately 13 mm from the pupil edge but central to the equatorial region of the lens, to contract the lens capsular membrane and restore the accommodative potential.

* * * * *

UNITED STATES PATENT AND TRADEMARK OFFICE
CERTIFICATE OF CORRECTION

PATENT NO. : 6,197,018 B1
DATED : March 6, 2001
INVENTOR(S) : O'Donnell, Francis E., Jr.

It is certified that error appears in the above-identified patent and that said Letters Patent is hereby corrected as shown below:

Column 4, claim 1,
Line 20, after "directed" insert -- to the basement capsular membrane --.

Signed and Sealed this

Twentieth Day of November, 2001

Attest:

NICHOLAS P. GODICI
Attesting Officer     Acting Director of the United States Patent and Trademark Office